United States Patent [19]

Ohtomo et al.

[11] Patent Number: 4,710,378
[45] Date of Patent: Dec. 1, 1987

[54] LYOPHILIZED HEPATITIS B VACCINE

[75] Inventors: Nobuya Ohtomo; Kyosuke Mizuno; Fukusaburo Hamada; Hiroshi Mizokami, all of Kumamoto, Japan

[73] Assignee: Juridical Foundation The Chemo-Sero-Therapeutic Research Institute, Kumamoto, Japan

[21] Appl. No.: 709,705

[22] Filed: Mar. 8, 1985

[30] Foreign Application Priority Data

Mar. 13, 1984 [JP] Japan ................................ 59-48669

[51] Int. Cl.$^4$ ............................................. A61K 39/29
[52] U.S. Cl. ........................................................ 424/89
[58] Field of Search ................................ 424/85-89; 435/68

[56] References Cited

U.S. PATENT DOCUMENTS 4,164,565  8/1979  Prince et al. ................. 435/172.1
4,565,697  1/1986  Ohmura et al. ................. 435/236

FOREIGN PATENT DOCUMENTS 101617  2/1984  European Pat. Off. .

OTHER PUBLICATIONS

Valenzuela et al., Cold Spring Harbor Laboratory Modern Approches to Vaccines, pp. 209-213, 1984.
Valenzuela et al., Nature, vol. 298, pp. 347-350, 1982.

*Primary Examiner*—Blondel Hazel
*Attorney, Agent, or Firm*—Wegner & Bretschneider

[57] ABSTRACT

Lyophilized preparation of hepartitis B vaccine, which comprises a purified hepatitis B virus surface antigen produced by a recombinant organism being capable of producing HBs antigen, which is adsorbed on aluminum gel in the lyophilized state in the presence of a stabilizer, said lyophilized preparation being prepared by the steps of adding an aluminum gel and a stabilizer to a purified recombinant-origin HBs antigen and lyophilizing the mixture. Said lyophilized preparation being able to be stably kept for a long period of time without losing its antigen titer and being useful for the prophylaxis of infection of hepatitis B virus.

3 Claims, No Drawings

LYOPHILIZED HEPATITIS B VACCINE

The present invention relates to a lyophilized preparation of hepatitis B vaccine. More particularly, it relates to a lyophilized preparation of hepatitis B vaccine which is prepared by subjecting a purified product obtained from HBs antigen to lyophilization in the presence of aluminum gel and a stabilizer, said HBs antigen being expressed by a transformed organism being capable of producing HBs antigen which is prepared by a conventional DNA recombination technique.

Hepatitis B is a disease which is induced by a hepatitis B virus (hereinafter, referred to as "HBV") and includes immunologically and clinically very serious problems, but there has never been found any effective therapeutic method therefor, and hence, prophylactic method has mostly been studied. Suitable prophylaxis is a method of applying a vaccine comprising as an effective ingredient HBs antigen to persons who are afraid to be infected by HBV. A vaccine has already been in practical use, which is prepared by highly purifying an HBs antigen obtained from a blood plasma of latent virus carriers who are usually called as merely "carrier", and inactivating the purified HBs antigen.

However, the blood-origin vaccine is obtained from blood plasma of HBs antigen-positive persons, and hence, it has various problems for the preparation thereof, such as difficulty to get a sufficient amount of the starting blood plasma; necessity of safety test in chimpanzee in order to prove no remaining of infectious factors such as hepatitis B virus or any other blood-origin viruses in the preparation; and difficulty to get sufficient chimpanzees for the test.

In order to eliminate such problems, many researchers have been studied on technique for obtaining a large amount of the starting HBs antigen by introducing an HBV DNA encoding the HBs antigen protein into *Escherichia coli* or an yeast by means of a DNA recombination technique and then expressing the HBs antigen by the transformed microorganisms thus obtained. Recently, the expression of HBs antigen with these recombinant microorganisms has been succeeded. Particularly, the production of HBs antigen with a recombinant yeast has been accomplished in an industrial scale, and then, it has been tried to purify the HBs antigen thus obtained and to prepare a hepatitis B vaccine preparation therefrom.

Hepatitis B vaccine is effective for prophylaxis of infection of the virus in people engaged in medical works, researchers who occasionally contact with hepatitis B patients and latent virus carriers as well as families of the patients and carriers and babies, wherein the virus is infected via blood. It is said that the carriers are usually found in the rate of 2 to 3% of total population in Japan and 10 to 15% in Southeast Asia and also in Africa. Thus, it is required to make avalable the hepatitis B vaccine worldwidely. From this viewpoint, it is necessary to make widely available the hepatitis B vaccine in the world including Japan, and it is essential to provide a preparation which is stable and can be kept for a long period of time.

The commercially available hepatitis B vaccine is a liquid preparation which is obtained from blood-origin HBs antigen product, and it loses gradually its antigen titer during the storage.

Under the circumstances, the present inventors have studied on a method for preparing hepatitis B vaccine having greater storage stability for a long period of time in an industrial scale, and have found that the desired vaccine can be obtained by using a recombinant-origin HBs antigen instead of the blood-origin HBs antigen and lyophilizing the HBs antigen under specific conditions.

It is known that an inactivated vaccine is usually prepared by incorporating as an adjuvant, for example, aluminum gel, in order to enhance the productivity of antibody within the body when the vaccine is administered. Hepatitis B vaccine preparations are also usually incorporated by aluminum gel. In case of a lyophilized preparation of hepatitis B vaccine, if the hepatitis B vaccine is made by lyophilizing HBs antigen only, it must be prepared by previously dissolving HBs antigen (hereinafter, occasionally referred to as "HBsAg") in a saline solution for injection or distilled water for injection and mixing the solution with aluminum gel before use. In such a method, adsorption of HBsAg onto aluminum gel varies in each minimum usage unit vessel depending on order of steps for the preparation, temperature, conditions for shake-mixing, etc. and hence the productivity of antibody may possibly vary in each vaccine. Besides, when a recombinant-origin HBs antigen is lyophilized under the same conditions as used for the conventional liquid preparation, the antigen titer of vaccine is undesirably decreased during the lyophilization.

The present inventors have intensively studied on the lyophilization conditions of recombinant-origin HBsAg adsorbed on aluminum gel, which do not show such problems as lowering of antigen titer or deterioration of properties, but can give the desired lyophilized preparation having greater storage stability than the conventional liquid preparations, and further studied on the composition for the suitable stable preparation. As a result, it has been found that the desired lyophilized preparation can be prepared by adsorbing purified recombinant-origin HBsAg onto aluminum gel in a suspension state, dissolving a stabilizer and optionally a preservative in the suspension, and then lyophilizing the mixture.

An object of the present invention is to provide an improved lyophilized preparation of hepatitis B vaccine by using recombinant organisms being capable of producing HBs antigen. Another object of the invention is to provide a lyophilization method of a recombinant-origin HBs antigen for giving a lyophilized hapatitis B vaccine having excellent storage stability. These and other objects and advantages of the invention will be apparent to skilled person from the following description.

The lyophilized hepatitis B vaccine of the present invention can be prepared by adding aluminum gel to an aqueous solution of an almost neutral buffer solution of the recombinant-origin HBs antigen to make adsorbed the HBs antigen onto the aluminum gel, adding thereto a stabilizer selected from amino acids and/or saccharides and optionally colloidal substances and further optionally a conventional preservative, an isotonic agent, etc. to prepare a vaccine solution, and lyophilizing it, preferably after being dividedly poured into minimum usage unit vessel. The lyophilized hepatitis B vaccine preparation thus obtained can keep the high antigen titer for a long period of time, and each minimum usage unit vessel show the same antigen titer in each preparation lot, and hence, it is very convenient for use thereof.

The starting purified recombinant-origin HBs antigen can be prepared by introducing a gene encoding HBs antigen isolated from hepatitis B virus DNA into organisms such as *E. coli*, yeasts, cultured cells of animals, etc., whereby transforming the organisms by the gene, and expressing the HBs antigen by acting of the HBs antigen gene. The method for preparing the recombinant-origin HBs antigen has already been known. For instance, a method of the preparation of a recombinant yeast-origin HBs antigen is reported by Valenzuela (cf. Valenzuela, Nature, 298, 347 (1982) and Japanese Patent First Publication No. 77823/1983), which comprises preparing a shuttle vector (pHBs 16) wherein an HBs gene is bound into a yeast alcohol dehydrogenase promoter in a shuttle vector (pMA 56) having a replication initiating region of pBR 322 plasmid, a replication initiating region of 2μ plasmid, Trpl, and an yeast alcohol dehydrogenase promoter region, introducing the shuttle vector into an yeast to prepare a transformed yeast, and culturing the transformed yeast to produce the desired HBs antigen.

Other known method for preparing an yeast-origin HBs antigen is reported by Miyanohara et al. (cf. Proc. Natl. Acad. Sci., USA, 80, 1 (1983) and Japanese Patent First Publication No. 31799/1984), which comprises preparing a shuttle vector (pAH 203) wherein an HBs gene is bound into a repressible acid phosphatase promoter in a shuttle vector (pAM 82) having a replication initiating region of 2μ plasmid, a replication initiating region of pBR 322 plasmid, a replication initiating region of an yeast chromosome, leu 2 gene of an yeast participating in leucine synthesis, an ampicillin-resistant gene of *E. coli*, and a region of a repressible acid phosphatase promoter of an yeast, introducing the shuttle vector into an yeast [AH 22 (a, leu2, his4, Can1, Cir+)] to prepare a transformed yeast, and culturing the transformed yeast to produce the desired HBs antigen.

It is also reported by Hitzeman that a shuttle vector wherein an HBs gene is bound into an yeast 3-phosphoglyceric acid kinase (PGK) promoter is prepared and then is used for preparing a transformed yeast which can produce an HBs antigen [cf.Hitzeman, Nucleic Acids Research, 11 (9), 2745 (1983) and Japanese Patent First Publication No. 109427/1983].

It is further reported by Nozaki et al. that a recombinant DNA is prepared by recombining an HBs gene with a vector having a replication initiating region of SV40 DNA inserted into an *E. coli* plasmid origined from Coll El, pMB1 or p15A and being defecient in a region of inhibiting replication in mammalian cells, and a transformed mammalian cells are obtained by transforming the mammalian cells, e.g. mouse LTK− cells with the recombinant DNA, and then, the transformed cells are cultured to obtain the desired HBs antigen [cf. 30th Plenary Session of The Society of Virology, Japan, Abstracts, P-1069 (1982) and Japanese Patent First Publication No. 36698/1984]. There are various other reports of producing HBs antigen by animal cells utilizing DNA recombination techniques, e.g. Japanese Patent First Publication Nos. 56685/1983, 995/1983 and 39784/1982.

The HBs antigen thus obtained is highly purified by conventional purification methods which are usually used for isolation and purification of biological active substances, such as cell fracture, extraction of the fractured cells, salting out with ammonium sulfate, gel fitration, ion exchange chromatography, fractionation with polyethylene glycol, affinity chromatography, ultracentrifugation with sucrose and cesium chloride, or the like, and the highly purified HBs antigen is used for the preparation of the lyophilized hepatitis B vaccine of the present invention.

The purified HBs antigen obtained from the recombinant organisms as above is subjected to lyophilization in the following manner. The HBs antigen is dissolved in water or in an about neutral buffer solution having a suitable concentration, such as 0.01M phosphate buffer, 0.01M citrate buffer, or 0.005M McIlvaine's buffer so as to have the following concentration of the HBs antigen and other additives.

That is, the HBs antigen is contained in a concentration of a protein of not more than 0.1 W/V %, preferably not more than 0.02 W/V %. The aluminum gel to be added as an adjuvant is contained in an amount of 3 to 10 times by weight as much as the weight of the HBs antigen (as the concentration of protein).

The adsorption of HBsAg onto aluminum gel is carried out by mixing an HBs antigen-containing solution with an aluminum gel, or by adding an appropriate amount of an aluminum chloride-containing solution to an HBs antigen-containing solution, and adding thereto an aqueous sodium hydroxide solution having an appropriate concentration, by which aluminum hydroxide gel is produced and simultaneously HBs antigen is adsorbed thereto. When an aqueous trisodium phosphate solution is used instead of the aqueous sodium hydroxide solution, aluminum phosphate gel is produced and thereto HBs antigen is adsorbed. Thus, the aluminum gel used in the present invention includes aluminum hydroxide gel and aluminum phosphate gel.

The HBs antigen-adsorbed aluminum gel suspension thus obtained is mixed with a stabilizer and optionally a preservative and an isotonic agent, and then, the mixture is lyophilized.

The stabilizer includes amino acids and polysaccharides. The amino acids and polysaccharides may be used either one alone, but preferably both are used together. Colloidal substances may also optionally be added as a stabilizer.

Suitable examples of the amino acids are glycine, alanine, glutaminic acid, arginine, lysine, etc. or a salt thereof (e.g. monosodium glutamate). They may be used alone or in combination of two or more thereof, and they are usually used in an amount of 0.1 to 2.0 W/V %. Suitable examples of saccharides are monosaccharides such as glucose, xylose, galactose, fructose, etc., disaccharides such as lactose, maltose, saccharose, etc., and sugar alcohols such as mannitol, sorbitol, xylitol, etc., which may be used alone or in combination of two or more thereof. They are usually used in an amount of 0.1 to 15 W/V %. Suitable examples of colloidal substances are gelatin, human albumin, dextrane, etc. They are usually used in an amount of 0.01 to 0.1 W/V %. Optionally a preservative such as thimerosal is used in an amount of about 0.05 to 0.1 W/V %.

The preparation is preferably incorporated by a neutral salt in order to make physiologically isotonic when the lyophilized vaccine is used. The neutral salt includes sodium chloride, potassium chloride, magnesium chloride. Preferred neutral salt is sodium chloride which may be used in a mixture of other neutral salts as mentioned above. The neutral salts are usually contained in a concentration of 0.1 to 3 W/V %, preferably 0.5 to 2 W/V %.

The thus prepared vaccine solution is divided and poured into vessels for each dosage unit package so that each vessel contains the HBs antigen in an amount of 20 μg to 1,000 μg. The divided solution in each vessel is lyophilized by conventional rapid lyophilization method or slow lyophilization method to give the desired lyophilized preparation. The lyophilization is usually carried out under the following conditions. That is, the solution is subjected to a pre-lyophilization at a low temperature (e.g. −40° C. or lower, preferably −50° C. or lower) under atmospheric pressure for several hours (e.g. 3 to 10 hours), and then subjected to first lyophilization at a fixed higher temperature (e.g. 0° to 8° C.) under a reduced pressure (e.g. 0.01 to 0.05 Torr) for ten to a few tens of hours (e.g. 15 hours), at which stage the temperature of the product becomes lower than −35° C. (e.g. about −38° C.). Thereafter, the product is subjected to second lyophilization at a fixed elevated temperature (e.g. 25° to 30° C.) under a more reduced pressure (e.g. 0.001 to 0.005 Torr) for several hours to a few tens of hours (e.g. 6 to 10 hours, preferably 7 to 9 hours).

The lyophilized preparation contains at least recombinant-origin HBs antigen, aluminum gel, a stabilizer, and a neutral salt.

The lyophilized preparation of hepatitis B vaccine thus obtained can be kept with good storage stability without lowering of antigen titer and further can be dissolved rapidly in an injection solution when used.

When the lyophilized preparation of the present invention is used, it is dissolved in distilled water for injection or physiological saline solution for injection so as to regulate the HBs antigen protein concentration to 5 μg/ml to 50 μg/ml and to regulate the salt concentration to approximately isotonic, and the physiologically isotonic solution is administered in subcutaneous route. The dose of the vaccine is usually in the range of 5 μg to 50 μg as HBs antigen protein for one administration in adult.

The preparation of the present invention shows no abnormal toxicity when tested in accordance with general test method in guinea pig as defined in Minimum Requirement of Biological Products (Notification No. 287, issued by Ministry of Health and Welfare, Japan, in 1981).

The present invention is illustrated by the following Reference Examples and Examples but should not be construed to be limited thereto.

REFERENCE EXAMPLE 1

Preparation of a purified HBs antigen origined from a recombinant yeast

In accordance with the method of Miyanohara et al. (cf. Japanese Patent First Publication No. 31799/1984), a recombinant yeast is prepared and is cultured to produce HBs antigen, and the HBs antigen is separated and purified as follows.

(1) Preparation of HBV DNA (i) Preparation of virus DNA

A pooled blood plasma (700 ml) obtained from ten persons (subtype adr) who are positive in HBsAg and HBeAg is centrifuged at 5,000 r.p.m. for 20 minutes to remove undissolved materials. The resulting solution is centrifuged at 4° C., 18,000 r.p.m. for 8 hours, and the resultant precipitates are re-dissolved in 10 ml of a buffer (pH 7.5) of 10 mM Tris-HCl, 0.1M NaCl and 1mM EDTA. The solution is added to the top of a centrifugal tube containing 30% sucrose, which is centrifuged at 4° C., 39,000 r.p.m. for 4 hours. The resultant precipitates are re-dissolved in the same buffer as above.

The buffer solution is subjected to the reaction by HBV DNA polymerase by treating it in a mixture (500 μl) of 67 mM Tris-HCl (pH 7.5), 80 mM NH$_4$Cl, 25 mM MgCl$_2$, 0.5% (W/V %, hereinafter, the same) NP40 (tergitol, manufactured by Sigma Co.), 0.1% 2-mercaptoethanol, 330 μM dCTP (deoxycytidine triphosphate), dGTP (deoxyguanosine triphosphate), and dATP (deoxyadenosine triphosphate), 0.5 μM α-[$^{32}$P]dTTP (deoxythymidine triphosphate) at 37° C. for 30 minutes. To the reaction mixture is added dTTP in a final concentration of 330 μM, and the mixture is further reacted at 37° C. for 3 hours, and to the reaction mixture is added the same volume of 100 mM EDTA solution. By the above DNA polymerase reaction, single-stranded region of the DNA is repaired to wholly double-strand to give a [$^{32}$P] labeled material. This material is added to the top of a centrifugal tube wherein 30%, 20% and 10% aqueous solutions of sucrose are layered in this order, and it is centrifuged at 4° C., 39,000 r.p.m. for 4.5 hours.

In order to digest the proteins strongly bonded to DNA, the precipitates obtained above are treated in a mixture (200 μl) of 1 mg/ml of pronase E (manufactured by Kaken Kagaku K.K.) and 0.2% aqueous sodium lauryl sulfate solution at 37° C. for 2 hours. The resulting mixture is extracted with phenol (200 μl) twice, and the resulting DNA-containing extract is washed with ether to remove phenol solvent to give a solution of HBV DNA. The DNA thus obtained has a specific radioactivity of $2.5 \times 10^6$ cpm/μg and can be used for digestion with restriction enzymes.

(ii) Cloning of HBV DNA

The double-stranded circular HBV DNA obtained above is cloned by using λ-phage Sharon 16A DNA as a vector and then is again cloned by using the known plasmid pACYC177 as a vector as follows.

(A) Cloning in the system of λ-phage Sharon 16A host-vector:

HBV DNA (20 ng) is treated with endonuclease Xho I in a mixture (20 μl) of 10 mM Tris-HCl (pH 7.4), 7 mM MgCl$_2$, 100 mM NaCl and 7 mM 2-mercaptoethanol at 37° C. for 2 hours. The resulting mixture is extracted with phenol (20 μl) and further with ether, and to the aqueous layer is added a double volume of cooled ethanol to precipitate DNA. The mixture is kept at −70° C. for one hour and then centrifuged at 10,000 r.p.m. for 5 minutes, and the precipitated DNA is recovered. The precipitates thus separated are dissolved in a mixture (5 μl) of 10 mM Tris-HCl (pH 7.4) and 1 mM EDTA. The HBV DNA and an equimolar amount of λ-phage Sharon 16 A DNA (having one recognition site of Xho I) obtained by cleavage with endonuclease Xho I in the same manner as above are reacted with T4 DNA ligase [a mixture (10 μl) of 50 mM Tris-HCl (pH 7.4), 10 mM MgC$_2$, 10 mM dithiothreitol, 100 μg/ml calf serum albumin, 0.5 mM ATP and 0.5 μl enzyme preparation (T4 ligase, manufactured by Takara Biomedicals, $1-5 \times 10^3$ unit/ml)] at 4° C. for 18 hours. The reaction mixture is extracted with phenol and ether and then subjected to precipitation with ethanol in the same manner as described above. The precipitates thus obtained are dissolved in a mixture (10 μl) of 10 mM Tris-HCl (pH 7.4) and 1 mM EDTA.

The thus annealed DNA is subjected to in vitro packaging operation to form λ-phage in the same manner as described in "Methods in Enzymology", 68, 299–309 and further plaques ($10^4$) are formed therefrom on an L-agar plate (23 cm×23 cm) by using *E. coli* DP50

SupF (cf. Blattner, F. R. et al, Science 196, 161, 1977) as an indicator. These plaques are subjected to plaque hybridization using $^{32}$P-labeled HBV DNA prepared above as a probe (cf. Science, 196, 180, 1977) in order to select plaques formed from the phage having HBV DNA, by which a plural of the desired phages are separated.

(B) Re-cloning by using plasmid pACYC177 as a vector:

From the phage having HBV DNA obtained in the above (A), a phage DNA is prepared by using *E. coli* DP50-SupF as a bacteria to be infected in the same manner as described in "Methods in Enzymology", 68, 245–378, 1979. The DNA thus obtained is digested with Xho I under the same conditions as described above for 2 hours, and the resulting reaction mixture is subjected to an electrophoresis with 0.75% agarose gel to isolate HBV DNA (3.2 kb). The HBV DNA is adsorbed onto DEAE (diethylaminoethyl cellulose) paper (manufactured by Toyo Roshi, Japan) in order to separate from the vector DNA and then eluted with 1M NaCl aqueous solution to give an HBV DNA having Xho I terminals at both ends.

Separately, plasmid pACYC177 (cf. Chang, A. C. Y., Cohen, S. N.; J. Bacteriol., 134, 1141–1156, 1978) having a single Xho I cleavage site within kanamycin-resistant gene thereof is digested with Xho I, and the product is purified by phenol extraction, ether treatment and ethanol precipitation in the same manner as described above.

The thus obtained pACYC177 cleaved with Xho I is mixed with XhoI-terminal HBV DNA obtained above in a molar ratio of 1:5, and covalently joined by a T4 DNA ligase-catalyzed reaction for 18 hours as described above.

The reaction mixture (10 μl) is added to 0.1 ml of *E. coli* λ1776 [cf. R. III. Curtiss, et al, "Molecular cloning of recombinant DNA" eds. W. A. Scott and R. Werner, page 99, Academic Press (1977)] which is prepared by the procedure as described in M. V. Norgard, Gene, 3, 279 (1978), and the mixture is mixed well and allowed to stand at 0° C. for 25 minutes. The mixture is applied onto an L-agar plate containing ampicillin (20 μg/ml), α-biotine (1 μg/ml), diaminopimelic acid (100 μg/ml) and thymine (20 μg/ml) and is incubated at 37° C. overnight. The resulting colonies are applied onto both an agar plate containing kanamycin (20 μg/ml) and an agar plate containing ampicillin (20 μg/ml), and the colonies which grow only on the agar plate containing ampicillin is selected. From the colonies thus selected, a plasmid is prepared by the procedure as described by K. Matsubara (J. Virol., 16, 479, 1975). The plasmid thus obtained, i.e. the recombinant DNA of pACYC177-HBV DNA (which is designated "pHBV"), is treated with Xho I under the same conditions as described above to give total HBV DNA fragment (3.2 kb).

(2) Preparation of shuttle vectors pAM82

An EcoRI fragment of about 8,000 nucleotide pair (8 kb) containing a polypeptide (P60) gene of 60,000 dalton which constitutes the repressible acid phosphatase (RAP) (available from Yeast S288C gene bank; cf. Clarke, L. and Carbon, J., Cell, 9, 91–99, 1976) is inserted into the EcoRI site of known *E. coli* plasmid pBR322 to give a plasmid, which is used as the starting material.

To remove coding sequence of RAP, the starting plasmid is digested with a restriction enzyme Sal I and covalently joined again with T4 DNA ligase. The resulting plasmid pAT25 is deficient from the Sal I site to the acid phosphatase gene fragment 5.2 kb [said plasmid pAT 25 being a plasmid consisting of a fragment (about 3.7 kb) of from EcoRI site to Sal I site of pBR322 which contains the ampicillin-resistant gene and a fragment (about 2.8 kb) of from EcoRI site to Sal I site of the yeast acid phosphatase gene, wherein both fragments link at each corresponding terminal thereof].

Into the EcoRI site of the above pAT 25 is inserted an EcoRI fragment (1.4 kb) containing ars 1 and Trp 1 gene which is prepared by treating a plasmid YRP 7 (cf. Struhl, K. et al, Proc. Natl. Acad. Sci. U.S.A., 76, 1035–1039, 1979) with EcoRI to give a plasmid pAT 26. Said ars 1-Trp 1 fragment has a single recognition site of a restriction enzyme Hind III within the Trp 1 gene.

Into the Hind III site of the above pAT 26 is inserted a Hind III fragment containing a Leu 2 and 2μ ori which is prepared by treating a plasmid pSLE 1 (cf. Tohe, A. et al, J. Bacteriol., 141, 413–416, 1980) with Hind III to give a shuttle vector pAT 77. The pAT 77 carried on *Saccharomyces cerevisiae* (i.e. *Saccharomyces cerevisiae* AH 22/pAT 77) has been deposited at Fermentation Research Institute, Agency of Industrial Science and Technology, Japan under Budapest Treaty as "FERM BP-324".

The pAT 77 thus obtained (1 μg) is cleaved with Sal I and then is treated with an exonuclease BAL 31 (0.1 U) in a solution (50 μl) of 20 mM Tris-HCl (pH 8.2), 12 mM CaCl$_2$, 12 mM MgCl$_2$, 0.2M NaCl and 1 mM EDTA for 30 seconds to one minute. The reaction mixture is subjected to phenol extraction and ethanol precipitation in the same manner as described above. The resulting precipitates are mixed with Xho I linker (1 pmol) and joined by T4 DNA ligase under the same conditions as described above for 12 hours.

*E. coli* α1776 is transformed with the above reaction mixture by the procedure as described in R. III. Curtiss et al, "Molecular cloning of recombinant DNA" eds. W. A. Scott and R. Werner, page 99, Academic Press (1977), and from the resulting transformants, plasmid DNAs are prepared by the procedure as described by K. Matsubara (J. Virol., 16, 479, 1975). According to Maxam-Gilbert method (cf. Maxam, A. & Gilbert, W.; Pro. Natl. Acad. Sci., 74, 560–564), the nucleotide sequence of the resulting DNAs is determined, and further, the region of the acid phosphatase gene deleted with BAL 31 is determined. Among these DNAs, the desired plasmids pAM 82 is selected and isolated.

Designating "A" in the codon ATG encoding the first amino acid (methionine) of the product P60 of the phosphatase structural gene as "+1", in the shuttle vector pAM 82, the region till-33 is deleted. The pAM 82 carried on *Saccharomyces cerevisiae* (i.e. *Saccharomyces cerevisiae* AH 22/pAM 82) has been deposited at Fermentation Research Institute, Agency of Industrial Science and Technology, Japan under Budapest Treaty as "FERM BP-313".

(3) Preparation of HBsAg gene-expression plasmids

HBV DNA obtained by treating a plasmid pHBV with Xho I is recombined with Xho I cleaved shuttle vector pAM 82 in the molar ratio of 5:1 by T4 DNA ligase under the same conditions as described above.

*E. coli* α1776 is transformed with the reaction mixture and a plasmid DNA is prepared from the resulting ampicillin-resistant transformant. The DNA thus prepared is analyzed with various restriction enzymes, such as Xho I, Xba I and Hind III, and thereby, insertion of HBV DNA into the vectors and direction thereof are determined.

The thus obtained HBsAg gene-expression plasmid (designated pAH 203) has HBs gene and HBc gene in this order downstream the phosphatase promoter, which is an HBs Ag-expressing plasmid.

(4) Preparation of transformed yeast

The starting yeast is *Saccharomyces cerevisiae* AH22 [a, leu2, his4, can1 (Cir+)], which has been deposited at Fermentation Research Institute, Agency of Industrial Science and Technology, Japan under Budapest Treaty as "FERM BP-312". The starting yeast is inoculated in YPD medium (100 ml) consisting of 2% polypeptone, 1% yeast extract and 2% glucose, and the mixture is incubated at 30° C. overnight, and thereafter, the cells are collected by centrifugation. The cells thus collected are washed with sterilized water (20 ml), suspended in a solution (5 ml) of 1.2M sorbitol and 100 μg/ml zymolyase-60,000 (manufactured by Seikagaku Kogyo K.K., Japan), and the suspension is allowed to stand at 30° C. for 30 minutes to give spheroplast. The spheroplast thus prepared is washed with 1.2M sorbitol solution three times, and then suspended in a solution (0.6 ml) of 2M sorbitol, 10 mM $CaCl_2$ and 10 mM Tris-HCl (pH 7.5). The suspension thus prepared is divided into a small test tube in a volume of 60 μl. To the suspension is added the solution of the recombinant plasmid pAH 203 (30 μl) prepared in the above (3). After mixing well, 0.1M $CaCl_2$ (3 μl) is added thereto in a final concentration of 10 mM $CaCl_2$, and the mixture is allowed to stand at room temperature for 5 to 10 minutes. To the resulting mixture is added each 1 ml of a solution of 20% polyethylene glycol 4,000, 10 mM $CaCl_2$ and 10 mM Tris-HCl (pH 7.5), and the mixture is allowed to stand at room temperature for about 20 minutes. The resulting mixture (each 0.2 ml) is added to a medium (10 ml) consisting of 22% sorbitol, 2% glucose, 0.7% yeast nitrogen base amino acid, 2% YPD, 20 μg/ml histidine and 3% agar, which is kept at a constant temperature of 45° C. After gently mixing, the mixture is added in a layer onto a plate of minimal medium containing 1.2M sorbitol which is previously prepared and consists of 0.7% yeast nitrogen base amino acid, 2% glucose, 20 μg/ml histidine and 2% agar and is set thereon. The plate is incubated at 30° C. to give a colonie of a leucine-non-requiring yeast. The colonie is incubated in a BurkHolder minimal medium supplemented with histidine (20 μg/ml) [cf. Tohe, A, et al; J. Bachterol., 113, 727–738, 1973] to give the desired transformed yeast: *Saccharomyces cerevisiae* pAH 203.

(5) Production of HBsAg with the transformed yeast

The transformed yeast obtained in the above (4) is inoculated into BurkHolder minimal medium (10 ml) supplemented with histidine (20 μg/ml) and incubated at 30° C. The resulting culture is further inoculated into BurkHolder minimal medium (10 liters) supplemented with histidine (20 μg/ml) and incubated with stirring at 30° C. for 48 hours. The cells in logarithmic growth phase are collected by centifugation, suspended in a minimal medium (10 liters) containing no phosphate (which is prepared by replacing $KH_2PO_4$ in Burk-Holder minimal medium with KCl, followed by supplementing with 20 μg/ml histidine) in a cell concentration of about $4 \times 10^6$ cells/ml. After incubating at 30° C. for about 24 hours, the culture medium is centrifuged at 4,000 r.p.m. for 10 minutes to collect the cells (about 120 g).

(6) Preparation of purified product of HBs antigen

To the cells (about 1 kg) obtained by repeating the procedure as in the above (5) is added 0.1M phosphate buffer (pH 7.2) (5 liters), and the mixture is treated with a Manton-Gaulin fracturing machine under a pressure of 600 to 700 kg/cm² to fracture the cells. The fractured cells are centrifuged to remove course pieces of the fractured cells to give a crude extract of HBs antigen. The crude extract is regulated to pH 5.2 by adding dropwise a 10% aqueous acetic acid. After the mixture is stirred at 4° C. for about 30 minutes, the resulting precipitates are removed by centrifugation.

To the supernatant thus obtained is added aqueous ammonia to regulate the mixture to about pH 6.5, and thereto is added slowly ammonium sulfate so that the final concentration becomes 2.5M, while keeping the pH value as above. After allowing to stand for about 30 minutes, the mixture is centrifuged to take out precipitates containing HBs antigen. The precipitates thus obtained are suspended in 0.1M phosphate buffer (pH 7.2) (about 300 ml), and the mixture is dialyzed against the same buffer as used above.

After the dialysis, the mixture is diluted about 3 folds with 0.1M phosphate buffer, and then passed through a column packed with a hydroxyapatite (gel content: about 1 liter) which column is previously equilibrated with the same buffer as above, by which HBs antigen is adsorbed onto the gel. The column is washed well with the same buffer as used for the equilibration, and then, 0.2M potassium phosphate buffer (pH 7.2, about 3 liters) is passed through the column to remove contaminants. Thereafter, 0.5M potassium phosphate buffer (pH 7.2, about 3 liters) is passed through the column to elute HBs antigen. After dialyzing against 0.1M potassium phosphate buffer, the HBs antigen-containing fraction is passed through a column packed with hydroxyapatite (gel) content: about 500 ml) which column is previously equilibrated with the same buffer as above, by which HBs antigen is adsorbed onto the gel. The column is passed through with a potassium phosphate buffer (about 2 liters) having a concentration gradient of 0.2M→0.5M to collect a fraction containing HBs antigen.

The HBs antigen-containing fraction thus obtained (about 1000 ml) is dialyzed against 0.01M phosphate buffer and then concentrated until 100 ml with a hollow fiber ultrafilter (Minimodule, manufactured by Asahi Chemical, Japan).

A 50% sucrose solution, a 20% sucrose solution and the HBs antigen-containing fraction thus obtained are entered in three layers in a ultracentrifugation tube for Hitachi RP-42, and the tube is ultracentrifuged at 27,000 r.p.m. at 4° C. for 16 hours, by which HBs antigen is concentrated at around the interface of the sucrose solution layers.

The HBs antigen-containing fraction thus purified is dialyzed against 0.14M sodium chloride-added 0.01M phosphate buffer, and thereto is added cesium chloride in a concentration of 1.2 g/ml. The mixture is concentrated by subjecting to ultracentrifugation with Hitachi RP-42 ultracentrifuging machine at 25,000 r.p.m. at 10° C. for 60 hours to give purified HBs antigen. The HBs antigen-containing fraction thus purified is dialyzed against 0.14M sodium chloride-added 0.01M phosphate buffer, and then is concentrated with Minimodule (manufactured by Asahi Chemical). The resultant is further dialyzed against 0.14M sodium chloride-added 0.01M phosphate buffer, and then is sterilized by filtration to give a purified product of HBs antigen (HBs antigen protein content: 106 μg/ml; 12 ml).

According to SDS-polyacrylamide gel electrophoresis, the purified product of HBs antigen obtained above showed a single band of the subunit protein (molecular weight: about 25,000). Besides, when the purified product of HBs antigen was compared with a standard product of a human-origin HBs antigen according to an immuno-diffusion method using an anti-recombinant-origin HBs antigen-guinea pig antibody and an anti-human-origin HBs antigen-guinea pig antibody, both HBs antigen purified products showed identical antigenicity.

REFERENCE EXAMPLE 2

Preparation of a purified HBs antigen origined from recombinant mammalian cells

In accordance with the method of Nozaki et al. (cf. Japanese Patent First Publication No. 36698/1984), recombinant mammalian cells are prepared and are cultured to produce HBs antigen, and the HBs antigen is separated and purified as follows.

(1) Preparation of HBV DNA BamHI fragment

The plasmid pHBV prepared in the above Reference Example 1, (1) is treated with BamHI in a usual manner, and the reaction mixture is subjected to electrophoresis with 0.75% agarose gel to give a BamHI fragment of HBV DNA.

(2) Preparation of vector (pXRIIG BamHI fragment)

A shuttle vector pXRIIG (available at Harvard University, U.S.A.) (1 µg) is added to a mixture (20 µl) of 10 mM Tris-HCl (pH 8.0), 7 mM $MgCl_2$, 100 mM NaCl and 2 mM 2-mercaptoethanol, and thereto is added one unit of BamHI (one unit: an enzymatic activity being capable of completely digesting 1 µg of λ-DNA per one hour), and the mixture is reacted at 30° C. for one hour. The reaction mixture is extracted with phenol, and the aqueous layer is extracted with ether and then subjected to ethanol precipitation. The precipitates are dissolved in water. The solution is used in the preparation of a recombinant DNA.

(3) Preparation of a recombinant DNA of HBV DNA-pXRIIG

A solution (50 µl) containing HBV DNA BamHI fragment (150 ng) and pXRIIG BamHI fragment (50 ng) is reacted with T4 DNA ligase at 16° C. for 4 hours.

E. coli α1776 is transformed with the reaction mixture obtained above in the same manner as described above. From the resulting transformants, there are selecred colonies which grow on an agar medium after incubating on L-agar plate for 12 hours in the same manner as described in the above (1), (B), and the colonies thus selected are applied onto an agar medium containing tetracycline (Tc) (10 µg/ml) and an agar medium containing ampicillin (Ap) (40 µg/ml). The colonies (clones) which can not grow on the Tc-containing agar medium but can grow on the Ap-containing agar medium are selected. These clones are each incubated in the culture liquid of E. coli α1776 as mentioned above, and the plasmids are extracted in the same manner as described above. By analysis of the cleavage pattern with various restriction enzymes (e.g. BamHI, XhoI, Hind III, Sal I), there is selected a recombinant DNA consisting of three BamHI fragments of HBV DNA and one fragment of pXRIIG (said recombinant DNA being designated pSHB3).

(4) Transformation of mouse LTK− cells

The following liquid A and liquid B are prepared.

Liquid A: a solution (1.25 ml, pH 7.1) consisting of 50 mM Hepes (i.e. N-2-hydroxyethylpiperazine-N-2-ethanesulfonic acid), 280 mM NaCl, and 15 mM $Na_2HPO_4 \cdot 12H_2O$.

Liquid B: a mixture of DNA solution (1.1 ml) consisting of pSHB3 (50 µg), pTK (2.5 µg) (cf. ColbereGarapin, F., Proc. Natl. Acad. Scie. USA, 76, 3755, 1979), salmon spermatic DNA (carrier DNA) (50 µg) and 2M $CaCl_2$ (0.15 ml).

The liquid B is added dropwise with stirring to the liquid A, and the mixture is allowed to stand at room temperature for 30 minutes. After pipetting sufficiently, the mixture (0.5 ml) is added dropwise to a single layer of mouse LTK− cells (about $10^5$ cells/flask) in a flask. The flask is kept at room temperature for 30 minutes in order to make the mixture adsorbed into the cells, and thereto is added Dulbecco's modified Eagle's medium containing 10% calf serum (hereinafter, referred to as "DMEM", 5 ml) (cf. Dulbecco, R. & Freeman, G.; Virology, 8, 396, 1959), and the mixture is incubated under 5% $CO_2$ at 37° C. for about 5 hours. After exchanging with new DMEM, the mixture is further incubated for about 24 hours, and then, the medium is exchanged to a medium containing hypoxanthine (15 µg/ml), aminopterin (1 µg/ml) and thymidine (5 µg/ml) (hereinafter, referred to as "HAT medium") [cf. Littlefield; J. Proc. Natl. Acad. Sci. USA, 72, 3961–3965, (1963)]. The incubation is continued while the medium is exchanged with a new HAT medium every two to three days. After 4 weeks, the colonies of cells of TK+ are collected to give the desired transformed cells.

(5) Production of HBs antigen by transformed mammalian cells

The transformed mouse L cells as prepared in the above (4) is inoculated into a DMEM medium containing 10% calf serum, penicillin (250 units/ml) and streptomycin (0.2 µg/ml), and the mixture is incubated at 37° C. for one week. The supernatant of the culture broth contains HBs antigen in a concentration of about 400 ng/ml.

(6) Purification of HBs antigen produced by transformed mammalian cells

The culture supernatant (10 liters) obtained by repeating the culture as in the above (5) is concentrated until 1000 ml with a hollow fiber ultrafilter (Minimodule, manufactured by Asahi Chemical, Japan). To the solution is added gradually ammonium sulfate in a final concentration of 2.5M while keeping at pH 6.5 by adding aqueous ammonia. After allowing to stand for about 30 minutes, an HBs antigen-containing precipitates are separated by centrifugation. The precipitates thus obtained are dissolved in 0.14M sodium chloride-added 0.01M phosphate buffer (pH 7.2) (100 ml), and the mixture is dialyzed against the same buffer as used above.

After the dialysis, the mixture is subjected to gel filtration chromatography by passing through a column packed with sepharose CL6B (manufactured by Pharmacia, Sweden) (gel content: 2 liters). The HBs antigen-containing fraction (a fraction having the first peak from the initiation of elution corresponding to the volume of void, detecting by analysis with UV absorption monitor) is collected and pooled. The pooled fraction is dialyzed against 0.1M potassium phosphate buffer (pH 7.2), and then is passed through a column packed with hydroxyapatite (gel content: about 250 ml) which column is previously equilibrated with the same buffer as above, by which HBs antigen is adsorbed onto the gel. The column is washed with the same buffer for equilibration to remove the contaminants and then is treated with 0.5M potassium phosphate buffer to elute HBs antigen. The HBs antigen-containing fraction (about 250 ml) is dialyzed against 0.01M phosphate buffer (pH 6.2), and is concentrated until 50 ml with a hollow fiber ultrafilter.

A 50% sucrose solution, a 20% sucrose solution and the HBs antigen-containing fraction thus obtained are entered in three layers in a ultracentrifugation tube for Hitachi RP-42, and the tube is ultracentrifuged at 27,000 r.p.m. at 4° C. for 16 hours, by which HBs antigen is concentrated at around the interface of the sucrose solution layers.

The HBs antigen-containing fraction thus purified is dialyzed against 0.14M sodium chloride-added 0.01M phosphate buffer, and then is concentrated with Minimodule (manufactured by Asahi Chemical). The resultant is sterilized by filtration to give a purified product of HBs antigen (HBs antigen protein content: 98 μg/ml; 14 ml).

EXAMPLE 1

To a solution of a purified product of a recombinant-origin HBs antigen in the same manner as described in Reference Example 1 (HBs antigen protein concentration: 86 μg/ml) is added an aluminum hydroxide gel in an amount of 8 times by weight (calculated as the weight of aluminum hydroxide) as much as the weight of HBs antigen protein. This mixture is centrifuged and the supernatant is removed to give HBs antigen-adsorbed aluminum hydroxide gel.

Separately, the above procedure is repeated except that an aluminum phosphate gel is used instead of aluminum hydroxide gel to give HBs antigen-adsorbed aluminum phosphate gel.

To each HBs antigen-adsorbed aluminum gel obtained above are added solutions of various kinds of stabilizers as shown in Table 1 in 0.14M sodium chloride-added 0.01M phosphate buffer (pH 6.0) to give vaccine solutions (HBs antigen protein concentration: 40 μg/ml).

Each 1 ml of these solutions is packed in a 2 ml vial and is subjected to pre-lyophilization at −50° C., under atmospheric pressure for 6 hours, and after reducing the pressure to 0.04 Torr, subjected to the first lyophilization at 5° C. for 15 hours, and then subjected to the second lyophilization at 30° C., under a pressure of 0.04 Torr for 8 hours, by which the desired lyophilization preparation is obtained.

To the lyophylized product Run Nos. 1 to 11 was added a physiological saline solution (each 2 ml) and further added sodium citrate to dissolve completely aluminum gel. HBs antigen in the solution was measured by a radioimmunoassay method using AUSRIA II (manufactured by Dainabbott Radioisotope Lab., Japan), and the data were compared with reference (the product before being subjected to lyophilization). The relative antigenicity is shown in Table 2.

TABLE 1

| Run No. | Aluminum hydroxide (μg/ml) | Aluminum phosphate (μg/ml) | Glucose (μg/ml) | Lactose (μg/ml) | Mannitol (μg/ml) | Monosodium l-glutamate (μg/ml) | Arginine (mg/ml) | Lysine (mg/ml) | Glycine (mg/ml) | Alanine (mg/ml) | Gelatin (mg/ml) | Human albumen (mg/ml) |
|---|---|---|---|---|---|---|---|---|---|---|---|---|
| 1 | 320 | 0 | 0 | 0 | 0 | 0 | 0 | 0 | 0 | 0 | 0 | 0 |
| 2 | 320 | 0 | 100 | 0 | 0 | 0 | 0 | 0 | 0 | 0 | 0 | 0 |
| 3 | 320 | 0 | 100 | 0 | 0 | 2 | 2 | 0 | 0 | 0 | 0 | 0 |
| 4 | 320 | 0 | 100 | 0 | 0 | 2 | 2 | 0 | 0 | 0 | 0.4 | 0 |
| 5 | 320 | 0 | 0 | 100 | 0 | 2 | 2 | 0 | 0 | 0 | 0.4 | 0 |
| 6 | 320 | 0 | 0 | 0 | 100 | 2 | 2 | 0 | 0 | 0 | 0.4 | 0 |
| 7 | 320 | 0 | 0 | 0 | 100 | 2 | 2 | 0 | 0 | 0 | 0 | 1.0 |
| 8 | 320 | 0 | 0 | 0 | 100 | 2 | 0 | 2 | 0 | 0 | 0.4 | 0 |
| 9 | 320 | 0 | 0 | 100 | 0 | 0 | 0 | 0 | 10 | 0 | 0.4 | 0 |
| 10 | 320 | 0 | 0 | 100 | 0 | 0 | 0 | 0 | 0 | 10 | 0.4 | 0 |
| 11 | 0 | 320 | 0 | 100 | 0 | 2 | 2 | 0 | 0 | 0 | 0.4 | 0 |

TABLE 2

| Run No. | Relative antigenicity (*) |
|---|---|
| 1 | 0.16 |
| 2 | 0.66 |
| 3 | 0.82 |
| 4 | 1.05 |
| 5 | 0.98 |
| 6 | 0.96 |
| 7 | 1.04 |
| 8 | 0.96 |
| 9 | 1.02 |
| 10 | 0.94 |
| 11 | 0.99 |

(*) Relative value of the antigenicity of the lyophilized product to that of the product before lyophilized (the value of the latter is calculated as 1).

EXAMPLE 2

To a solution (120 ml) of a purified product of a recombinant-orgin HBs antigen (HBs antigen protein cocentration: 96 μg/ml) prepared in the same manner as described in Reference Example 1 is added an aqueous solution (5 ml) of aluminum chloride (60 mg). The solution is regulated to pH 6.1 with 1N NaOH. The mixture is centrifuged, and the a supernatant is removed to give an HBs antigen-absorbed aluminum gel. The aluminum gel thus obtained is mixed with a 0.14M sodium chloride-added 0.01M phosphate buffer (pH 6.0, 72 ml) containing lactose (10 W/V %), monosodium l-glutamate (0.4 W/V %), arginine (0.4 W/V %), gelatin (0.08 W/V %) and thimerosal (0.005 W/V %).

The vaccine solution thus obtained is divided and each solution (0.5 ml) is poured into a 2 ml vial, which is subjected to lyophilization treatment in the same manner as described in Example 1.

The lyophilized vaccine preparation obtained in the above Example 2 was compared with the starting stock in terms of immunogenicity in guinea pigs. That is, the lyophilized vaccine preparation was dissolved in distilled water, and the solution was subcutaneously injected on the back of guinea pigs in an innoculation amount of 0.5 μg, 1 μg and 2 μg of HBsAg. After 5 weeks, blood was collected from the animals, and the anti-HBs antibody thereof was measured by radioimmunoassay (using a kit for detecting anti-HBs antibody: AUSAB, manufactured by Dainabbott, Japan). As a reference, the antibody titer in case of innoculation of the starting stock was measured likewise. The results are shown in Table 3.

TABLE 3

|  | Relative titer (*) | 95% Confidense limits |
|---|---|---|
| Reference | 1.00 | |
| Lyophilized Vaccine | 3.78 | 2.15–14.21 |

(*) Average relative value of the average antibody value of the lyophilized vaccine in each injection amount to that of the starting stock (the value of the latter is calculated as 1).

The lyophilized vaccine was also tested as to the storage stability as follows.

After keeping lyophilized vaccine at a constant temperature for a fixed term, sodium citrate was added to the vaccine sample to dissolve aluminum gel, and then the antigenicity thereof was measured by a radioimmunoassay method. The relative value of the lyophilized product was calculated in comparison with a standard sample of HBs antigen (i.e. a product prepared by adding human albumin to a purified product of human-origin HBs antigen, dividing into a small portions in vials, which were kept in the state of being lyophilized at −80° C.; when measured, liquefied sample was used as a reference) (the antibody value of the reference being calculated as 1). The relative value of each sample is shown in Table 4 (wherein the value of the lyophilized sample is shown as 1).

The lyophilized products of the present inveniton were stable even after having been kept at 37° C. for 25 weeks, which was quite different from a liquid vaccine (cf. Comparative Example 1 disclosed hereinafter).

Besides, the samples which were kept at 37° C. for 25 weeks were tested as to abnormal toxicity, but any abnormal toxicity was observed.

TABLE 4

| Temperature for keeping | Change of antigenicity After keeping for: | | | | |
|---|---|---|---|---|---|
| | 1 week | 4 weeks | 10 weeks | 15 weeks | 25 weeks |
| 37° C. | 1.06 | 0.92 | 0.98 | 1.12 | 1.06 |
| Room temp. | 0.96 | 0.96 | 1.04 | 1.01 | 1 04 |
| 4° C. | 1.00 | 0.98 | 1.10 | 1.02 | 0.96 |

COMPARATIVE EXAMPLE 1

To a solution (50 ml) of the same purified product of a recombinant-origin HBs antigen as used in Example 2 (HBs antigen protein concentration 96 μg/ml) is added a suspension (2.9 ml) containing aluminum hydroxide gel (29 mg). The mixture is centrifuged, and the supernatant is removed to give an HBs antigen-adsorbed aluminum gel. The aluminum gel is mixed with a 0.14M sodium chloride-added 0.01M phosphate buffer (pH 6.0) (60 ml) containing thimerosal (50 μg/ml) to give a vaccine solution. The vaccine solution (each 1 ml) is divided into 2 ml vial to give a liquid vaccine preparation.

The vaccine preparation was tested as to the storage stability in the same manner as described in Example 2. The results are shown in Table 5.

Besides, the vaccine preparation as prepared in Example 2 was tested for the storage stability without being lyophilized (i.e. as it stands). The results are shown in Table 6.

TABLE 5

| Temperature for keeping | Change of antigenicity[1] After keeping for: | | | | |
|---|---|---|---|---|---|
| | 1 week | 5 weeks | 10 weeks | 15 weeks | 25 weeks |
| 37° C. | 0.71 | 0.20 | 0.18 | 0.03 | 0.00 |
| 4° C. | 1.02 | 1.09 | 0.98 | 1.02 | 1/02 |

[1]The method for the measurement is the same as in Example 2.

TABLE 6

| Temperature for keeping | Change of antigenicity[1] After keeping for: | | | | |
|---|---|---|---|---|---|
| | 1 week | 5 weeks | 10 weeks | 15 weeks | 25 weeks |
| 37° C. | 0.67 | 0.23 | 0.19 | 0.13 | 0.00 |

[1]The method for the measurement is the same as in Example 2.

EXAMPLE 3

To a solution (80 ml) of a purified product of a recombinant-orgin HBs antigen (HBs antigen protein concentration: 105 μg/ml) prepared in the same manner as described in Reference Example 2 is added an aqueous solution (5 ml) of aluminum hydroxide gel (50 mg). The mixture is centrifuged, and the supernatant is removed to give an HBs antigen-absorbed aluminum gel. The aluminum gel thus obtained is mixed with a 0.14M sodium chloride-added 0.01M phosphate buffer (pH 6.0, 105 ml) containing lactose (10 W/V %), glycine (1 W/V %), gelatin (0.05 W/V %) and thimerosal (0.005 W/V %).

The vaccine solution thus obtained is divided and each solution (1 ml) is poured into a 2 ml vial, which is subjected to lyophilization treatment in the same manner as described in Example 1.

The lyophilized product was tested as to the storage stability in the same manner as described in Example 2. The results are shown in Table 7.

TABLE 7

| Temperature for keeping | Change of antigenicity[1] After keeping for: | | | | |
|---|---|---|---|---|---|
| | 1 week | 5 weeks | 10 weeks | 15 weeks | 25 weeks |
| 37° C. | 1.01 | 0.97 | 1.06 | 0.99 | 0.98 |
| Room temp. | 1.04 | 0.95 | 1.05 | 1.00 | 0.98 |
| 4° C. | 1.04 | 0.92 | 1.11 | 0.97 | 1.01 |

[1]The method for the measurement is the same as in Example 2.

The sample kept at 37° C. for 25 weeks as used above was subjected to a test for abnormal toxicity, but any abnormal toxicity was observed.

What is claimed is:

1. A lyophilized preparation of hepatitis B vaccine, which comprises a purified hepatitis B virus surface antigen produced by a recombinant organism being capable of producing HBs antigen, which is adsorbed on aluminum gel in the lyophilized state in the presence of a stabilizer, said lyophilized preparation being prepared by the steps of adding an aluminum gel and a stablizer to a purified recombinant-origin HBs antigen and lyophilizing the mixture, wherein the stabilizer is a combination of at least one amino acid or a salt thereof, at least one saccharide or sugar alcohol and at least one colloidal substance.

2. The preparation according to claim 1, wherein the aluminum gel is a member selected from the group consisting of aluminum hydroxide gel and aluminum phosphate gel.

3. The preparation according to claim 1, wherein the amino acid or a salt thereof is a member selected from the group consisting of glycine, alanine, monosodium glutamate, arginine and lysine; the saccharide or sugar alcohol is a member selected from the group consisting of glucose, xylose, galactose, fructose, lactose, maltose, saccharose, mannitol, sorbitol and xylitol; and the colloidal substance is a member selected from gelation, human albumin and dextrane.

* * * * *